US010571385B2

United States Patent
Tat et al.

(10) Patent No.: US 10,571,385 B2
(45) Date of Patent: Feb. 25, 2020

(54) ULTRASONIC INSPECTION OF A STRUCTURE WITH A RAMP

(71) Applicant: The Boeing Company, Chicago, IL (US)

(72) Inventors: Hong Hue Tat, Redmond, WA (US); Barry Allen Fetzer, Renton, WA (US); Gary E. Georgeson, Tacoma, WA (US); William Joseph Tapia, Kapowsin, WA (US); Martin L. Freet, Federal Way, WA (US); Edward L. Puckett, Renton, WA (US)

(73) Assignee: The Boeing Company, Chicago, IL (US)

( * ) Notice: Subject to any disclaimer, the term of this patent is extended or adjusted under 35 U.S.C. 154(b) by 162 days.

(21) Appl. No.: 15/821,665

(22) Filed: Nov. 22, 2017

(65) Prior Publication Data

US 2019/0154561 A1    May 23, 2019

(51) Int. Cl.
*G01N 15/08* (2006.01)
*G01N 29/11* (2006.01)
*G01N 29/04* (2006.01)

(52) U.S. Cl.
CPC ......... *G01N 15/088* (2013.01); *G01N 29/043* (2013.01); *G01N 29/11* (2013.01); *G01N 2291/015* (2013.01); *G01N 2291/0231* (2013.01); *G01N 2291/056* (2013.01); *G01N 2291/106* (2013.01)

(58) Field of Classification Search
CPC .... G01N 15/088; G01N 29/043; G01N 29/11; G01N 2291/0231; G01N 2291/056
See application file for complete search history.

(56) References Cited

U.S. PATENT DOCUMENTS

| 4,502,331 | A | * | 3/1985 | Singh | G01N 29/07 73/627 |
| 4,803,639 | A | * | 2/1989 | Steele | G01N 23/18 378/4 |
| 9,176,099 | B2 | | 11/2015 | Motzer et al. | |
| 9,304,114 | B2 | | 4/2016 | Fetzer et al. | |
| 9,500,627 | B2 | | 11/2016 | Fetzer et al. | |
| 2008/0245151 | A1 | * | 10/2008 | Roney | F01D 25/285 73/628 |
| 2014/0305220 | A1 | | 10/2014 | Fetzer et al. | |

FOREIGN PATENT DOCUMENTS

| EP | 2031385 A1 | 3/2009 |
| GB | 2013344 A | 8/1979 |
| JP | 2011163814 A | 8/2011 |

OTHER PUBLICATIONS

European Patent Office Communication and Search Report, dated Mar. 22, 2019, regarding Application No. 18194165.9, 4 pages.

* cited by examiner

*Primary Examiner* — John E Chapman, Jr.
(74) *Attorney, Agent, or Firm* — Yee & Associates, P.C.

(57) ABSTRACT

A signal is sent into a structure at an angle substantially parallel to a ramp of the structure using a transducer array positioned at a first surface of the structure. An ultrasound response signal is formed at a second surface of the structure. The ultrasound response signal is received at the transducer array.

20 Claims, 9 Drawing Sheets

ULTRASONIC INSPECTION OF A STRUCTURE WITH A RAMP

BACKGROUND INFORMATION

1. Field

The present disclosure relates generally to inspecting structures, and more specifically, to structures with ramps. Yet more specifically, the present disclosure presents methods for ultrasonic inspection of portions of a structure beneath a ramp of the structure.

2. Background

Ultrasound is a non-destructive inspection method used in the inspection of structures, including composite structures. Ultrasonic inspections send ultrasonic signals into a structure and analyze ultrasonic ultrasound response signals to inspect the structure.

Ultrasonic inspection is sensitive to structural geometry. To inspect a structure using ultrasound, it is desirable for the front surface and back surface of the structure to be parallel to each other. For ultrasonic inspection it is desirable for the front surface and the back surface to be substantially smooth.

Structural designs having non-parallel surfaces or high surface roughness may be undesirably difficult to inspect with traditional ultrasonic inspection techniques. Therefore, it would be desirable to have a method and apparatus that takes into account at least some of the issues discussed above, as well as other possible issues.

SUMMARY

An illustrative embodiment of the present disclosure provides a method. A signal is sent into a structure at an angle substantially parallel to a ramp of the structure using a transducer array positioned at a first surface of the structure. An ultrasound response signal is formed at a second surface of the structure. The ultrasound response signal is received at the transducer array.

Another illustrative embodiment of the present disclosure provides a method. A signal is sent into a structure at an angle substantially parallel to a ramp of the structure using a transmitter positioned at a first surface of the structure. The signal is received at a second surface of the structure using a receiver to form a received signal, wherein the transmitter is separate from the receiver. An inconsistency is identified in the structure using the received signal.

A further illustrative embodiment of the present disclosure provides a method. A signal is sent into a structure at a first angle in which the first angle is a reflection of a second angle of a second ramp of the structure, in which the signal is sent into the structure using a transducer array positioned at a first surface of the structure. An ultrasound response signal is formed at a second surface of the structure. An ultrasound response signal is received at the transducer array. A porosity within a portion of the structure beneath the second ramp is detected using the amplitude of the ultrasound response signal.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account one or more different considerations. For example, the illustrative embodiments recognize and take into account that inspecting porosity in composite structures that are steeply angled/ramped, for example having greater than thirty degrees, is undesirably difficult. The illustrative embodiments recognize and take into account that currently, ply ramp areas that change at a rate less than 20:1 are inspected. Ply ramp areas that change at a rate less than 20:1 change at a rate less than three degrees. The illustrative embodiments recognize and take into account that structures with steeper ramps may be desirable.

The illustrative embodiments recognize and take into account that inspection requirements may need to be modified when a ramp in the structure has an angle greater than three degrees. The illustrative embodiments recognize and take into account that modifying inspection requirements may impact design of the structure. The illustrative embodiments recognize and take into account that increasing inconsistency detection near the ramp can enable improved design of structures.

The illustrative embodiments recognize and take into account that conventional ultrasonic inspections send signals into a structure at an angle perpendicular to a backwall, or second surface, of the structure. The illustrative embodiments recognize and take into account that for many structures, the signals may be sent into the structure substantially perpendicular to the first surface. The illustrative embodiments recognize and take into account that when a second surface is ramped or angled relative to a first surface, the signals may be directed at an angle relative to the first surface into the structure in order to be perpendicular to the second surface.

The illustrative embodiments recognize and take into account that for gently ramped areas (20:1), the process is to steer an ultrasonic beam perpendicular to the surface to be inspected. The illustrative embodiments recognize and take into account that for a steep angle, only a fraction of the sound path inspects the area of interest. Also, the illustrative embodiments recognize and take into account that steering the beam at steep angles is more difficult than desired.

Figure 1:
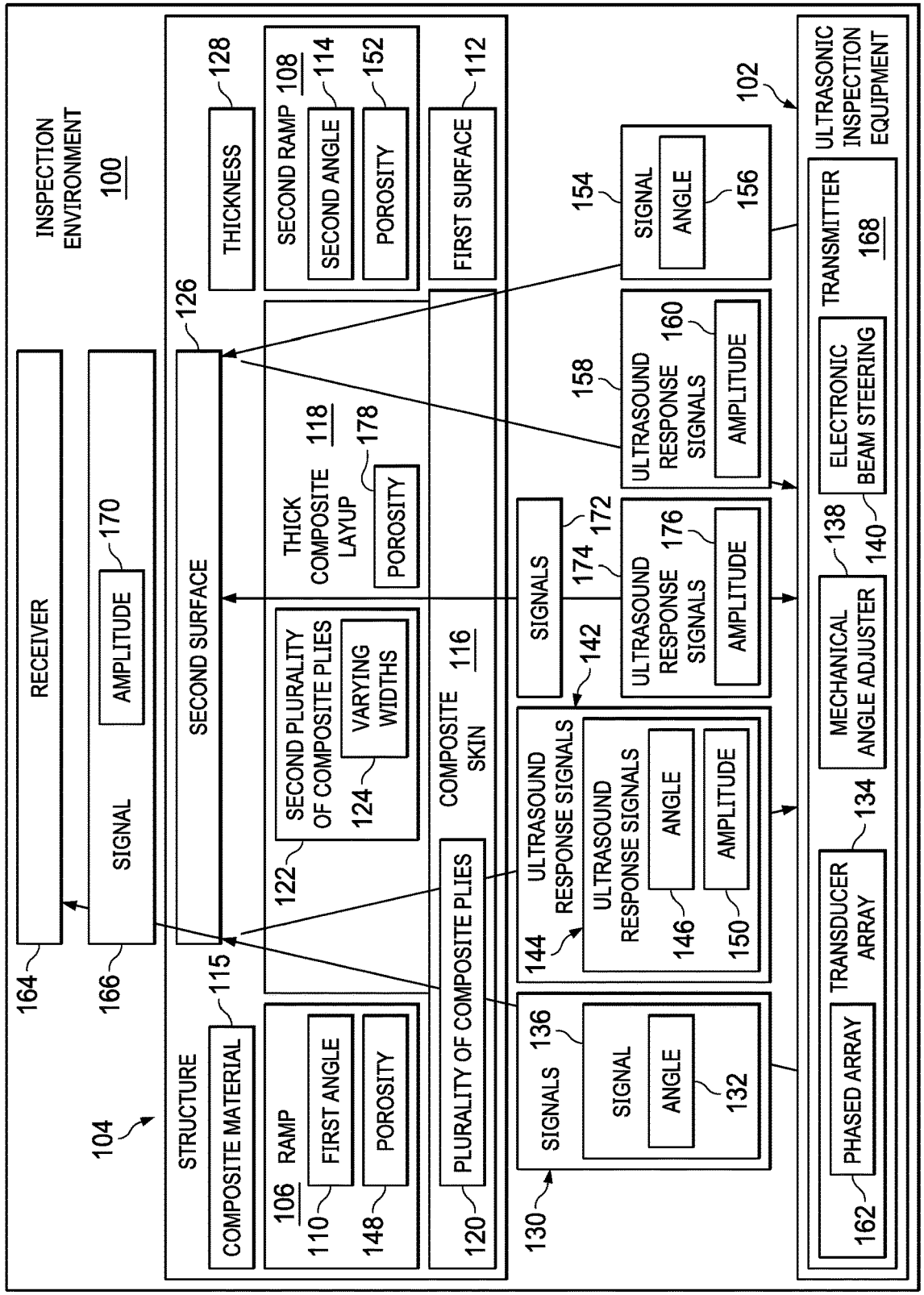
FIG. 1 is an illustration of a block diagram of an environment in which a composite structure is inspected using ultrasonic techniques in accordance with an illustrative embodiment.

Referring now to the figures and, in particular, with reference to FIG. 1, an illustration of a block diagram of an environment in which a composite structure is inspected using ultrasonic techniques in accordance with an illustrative embodiment. In inspection environment 100, ultrasonic inspection equipment 102 inspects structure 104. Structure 104 has ramp 106 and second ramp 108. Ramp 106 has first angle 110. First angle 110 is measured relative to first surface 112. First angle 110 is greater than three degrees. In some illustrative examples, first angle 110 is equal to or greater than sixty degrees.

Second ramp 108 has second angle 114. Second angle 114 is measured relative to first surface 112. Second angle 114 is greater than three degrees. In some illustrative examples, second angle 114 is equal to or greater than sixty degrees.

In some illustrative examples, structure 104 is formed of composite material 115. Structure 104 is formed by co-curing or co-bonding composite skin 116 and thick composite layup 118. Plurality of composite plies 120 are laid up to form composite skin 116. Second plurality of composite plies 122 of varying widths 124 are laid up to form thick composite layup 118.

Composite skin 116 and thick composite layup 118 are either co-cured or co-bonded to form structure 104 with ramp 106. Ramp 106 and second surface 126 are formed by curing thick composite layup 118.

Ramp 106 is created by varying widths 124 of second plurality of composite plies 122. Second ramp 108 is created by varying widths 124 of second plurality of composite plies 122.

To inspect structure 104 beneath ramp 106, ultrasonic inspection equipment 102 sends signals 130 into structure 104 at angle 132. Angle 132 is substantially parallel to first angle 110. To inspect the whole of structure 104 beneath ramp 106, angle 132 is desirably the same as first angle 110. However, some variations may occur in manufacturing of structure 104 or in operation of ultrasonic inspection equipment 102. As described herein, "substantially parallel" is within two degrees of another angle. Thus, angle 132 is within two degrees of first angle 110.

In some illustrative examples, ultrasonic inspection equipment 102 takes the form of transducer array 134. Transducer array 134 sends signals 130, such as signal 136, into structure 104 at angle 132 using mechanical angle adjuster 138 or electronic beam steering 140. Sending signals 130 and receiving ultrasound response signals 142 at transducer array 134 is referred to as "pulse echo inspection."

In some illustrative examples, ultrasound response signals 142 are formed at second surface 126 and are received at transducer array 134. For example, when signal 136 reaches second surface 126, ultrasound response signal 144 is formed at second surface 126. Ultrasound response signal 144 has angle 146. Angle 146 is a reflection of angle 132 about a line normal to second surface 126.

The reception of ultrasound response signals 142 takes into account angle 146. The reception of ultrasound response signals 142 is performed at an angle. This reception may be referred to as similar to "reverse" beam steering. The reception of ultrasound response signals is performed at a reflected angle to angle 132 either electronically or with a mechanical structure, such as a wedge.

After receiving ultrasound response signal 144, porosity 148 within structure 104 under ramp 106 is detected using amplitude 150 of ultrasound response signal 144. Amplitude 150 of ultrasound response signal 144 is used to detect a porosity within structure 104 in the paths followed by signal 136 and ultrasound response signal 144.

By repeatedly sending signals 130 into structure 104 and repeatedly receiving ultrasound response signals 142, porosity 148 is detected for multiple locations beneath ramp 106. In one illustrative example, by "stepping across" first surface 112, signals 130 are sent into different locations of structure 104 to detect porosity 148 for multiple locations beneath ramp 106. In another illustrative example, by sending signals 130 into structure 104 using different transmitters of phased array 162, signals 130 are sent into different locations of structure 104 to detect porosity 148 for multiple locations beneath ramp 106. In some illustrative examples, signals 130 are sent into different locations of structure 104 using a combination of stepping transducer array 134 across first surface 112 and using different transmitters of phased array 162.

In some illustrative examples, first angle 110 is a reflection of second angle 114. In these illustrative examples, signals 130 and ultrasound response signals 142 may be used to detect porosity 152 within structure 104 beneath second ramp 108. In these illustrative examples, although angle 132 is not parallel to second angle 114, angle 146 of ultrasound response signal 144 is parallel to second angle 114.

In other illustrative examples, signal 154 having angle 156 substantially parallel to second angle 114 is sent into structure 104 to detect porosity 152 within structure 104 beneath second ramp 108. In these illustrative examples, ultrasound response signal 158 forms at second surface 126. Amplitude 160 of ultrasound response signal 158 is used to detect porosity 152 within structure 104 beneath second ramp 108.

Ultrasound response signals 142 and ultrasound response signal 158 may be received by a transducer array 134, such as phased array 162. In other illustrative examples, signals 130 are received by receiver 164.

As depicted, signal 136 is sent into structure 104, and signal 166 is received by receiver 164. In these illustrative examples, signal 136 is sent into structure 104 using transmitter 168. Amplitude 170 of signal 166 received by receiver 164 may be used to detect porosity 148 within structure 104 beneath ramp 106. Receiving signal 166 at receiver 164 may be referred to as "through transmission" ultrasonic inspection.

At least one of signals 130 and signal 154 are sent into structure 104 to inspect structure 104 beneath ramp 106 and second ramp 108. As used herein, the phrase "at least one of," when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, "at least one of item A, item B, or item C" may include, without limitation, item A, item A and item B, or item B. This example also may include item A, item B, and item C, or item B and item C. Of course, any combination of these items may be present. In other examples, "at least one of" may be, for example, without limitation, two of item A, one of item B, and ten of item C; four of item B and seven of item C; or other suitable combinations.

In some illustrative examples, at least one of signals 130 or signal 154 are used to perform inspection sampling throughout structure 104. For example, signals 130 may be used to perform sampling throughout structure 104 including portions beneath second surface 126.

In some illustrative examples, signals 172 are sent into structure 104 normal to second surface 126 in portions of structure that are not ramped. Ultrasound response signals 174 are received normal to second surface 126. Amplitude 176 of ultrasound response signals 174 is used to detect porosity 178 within structure 104 between second surface 126 and first surface 112 of structure 104.

The illustration of inspection environment 100 in FIG. 1 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, at least one of ramp 106 or second ramp 108 has significant variation in average surface roughness. When ramp 106 has significant variation in surface roughness, ramp 106 may be referred to as having a rough surface. When second ramp 108 has significant variation in surface roughness, second ramp 108 may be referred to as having a rough surface.

Further, although porosity is discussed, ultrasonic inspection equipment 102 may be used to inspect for other types of inconsistencies. For example, signals 130 from ultrasonic inspection equipment 102 may be used to inspect for foreign object debris. When inspecting for foreign object debris, an associated time for ultrasound response signals 142 is used.

Figure 2:
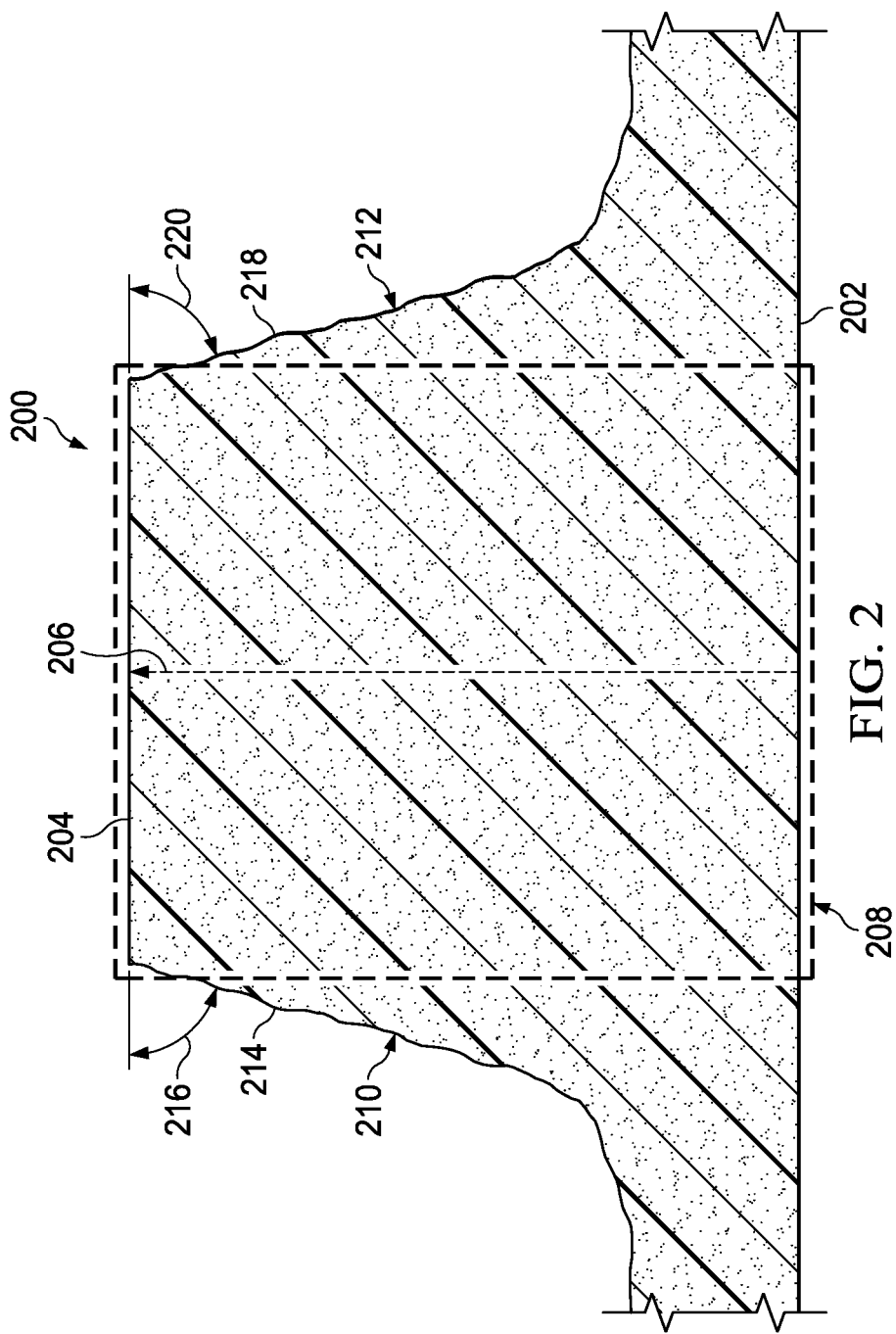
FIG. 2 is an illustration of a cross-sectional view of a composite structure in accordance with an illustrative embodiment.

Turning now to FIG. 2, an illustration of a cross-sectional view of a composite structure is depicted in accordance with an illustrative embodiment. Structure 200 is a physical implementation of structure 104 of FIG. 1.

Structure 200 has first surface 202 and second surface 204. Second surface 204 is parallel to first surface 202. Signals sent into first surface 202 travel in direction 206 and ultrasound response signals are reflected off of second surface 204. Ultrasonic inspection using signals normal to first surface 202 may be performed in region 208 of structure 200. First surface 202 is substantially planar. As depicted, second surface 204 is also substantially planar.

Structure 200 includes ramp 210 and ramp 212. Ramp 210 has rough surface 214. Angle 216 of ramp 210 relative to second surface 204 is greater than sixty degrees. An angle of ramp 210 relative to a line normal to second surface 204 is thirty degrees or less. Due to rough surface 214 and angle 216, traditional ultrasonic inspection is not performed on structure 200 beneath ramp 210.

Ramp 212 has rough surface 218. Angle 220 of ramp 212 relative to second surface 204 is greater than sixty degrees. An angle of ramp 212 relative to a line normal to second surface 204 is thirty degrees or less. Due to rough surface 218 and angle 220, traditional ultrasonic inspection is not performed on structure 200 beneath ramp 212.

The illustration of structure 200 in FIG. 2 is not meant to imply physical or architectural limitations to the manner in which an illustrative embodiment may be implemented. For example, ramp 210 and ramp 212 may have any desirable angle relative to first surface 202. For inspection using angled ultrasonic signals, ramp 210 and ramp 212 are each sixty degrees or more from first surface 202. When ramp 210 is sixty degrees or more from first surface 202, ramp 210 and a directed ultrasonic signal to inspect structure 200 below ramp 210 are each thirty degrees or less from a line normal to first surface 202.

Figure 3:
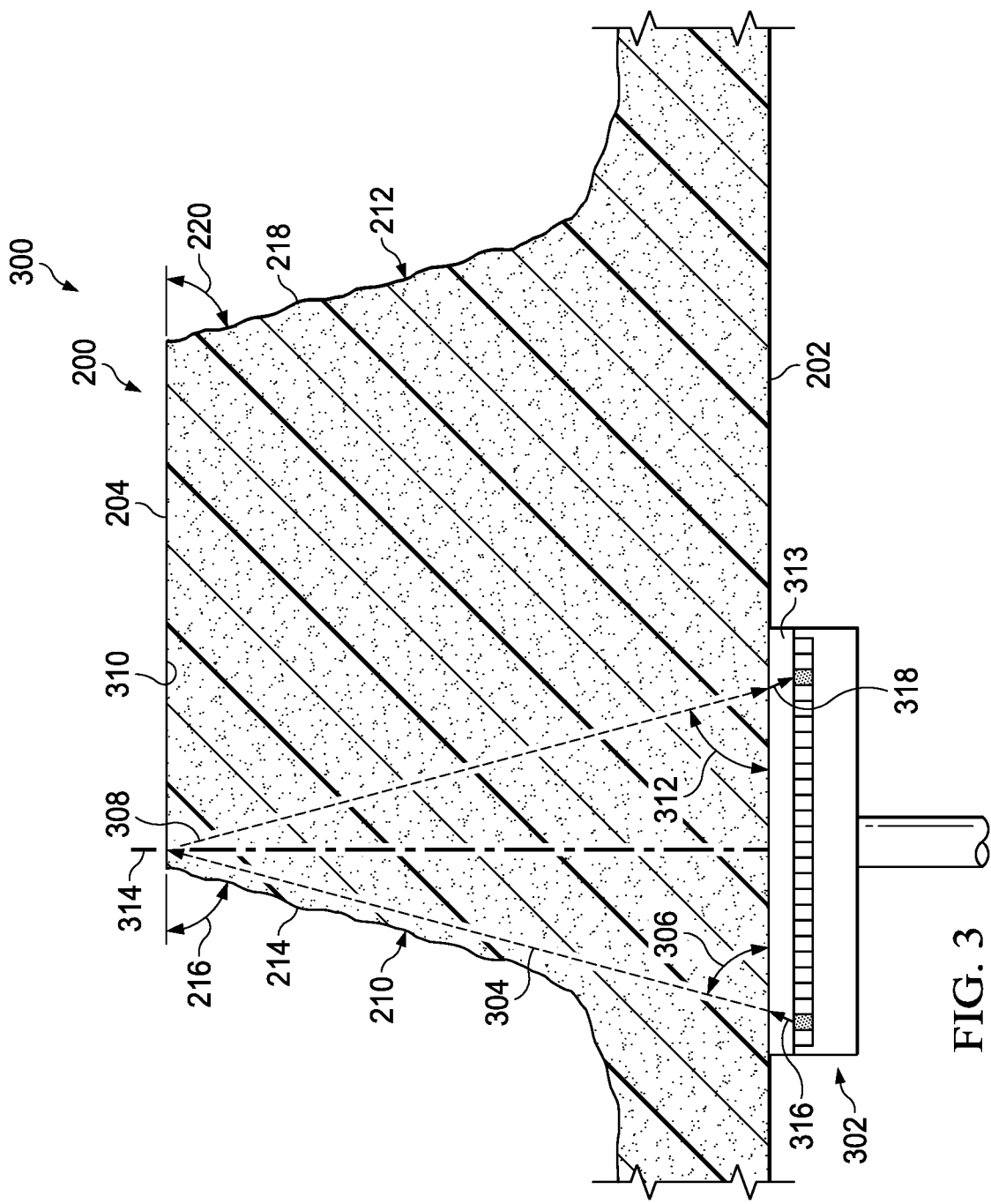
FIG. 3 is an illustration of a cross-sectional view of an ultrasonic inspection of a ramp of a composite structure in accordance with an illustrative embodiment.

Turning now to FIG. 3, an illustration of a cross-sectional view of an ultrasonic inspection of a ramp of a composite structure is depicted in accordance with an illustrative embodiment. View 300 is an illustration of an ultrasonic inspection of structure 200 of FIG. 2. In view 300, transducer array 302 sends signal 304 into first surface 202 of structure 200. Signal 304 is sent into structure 200 at angle 306 substantially parallel to ramp 210 of structure 200 using transducer array 302. As depicted, signal 304 is sent into structure 200 at angle 306 using electronic beam steering.

Transducer array 302 is a physical implementation of transducer array 134. FIG. 3 depicts a "pulse echo inspection." Transducer array 302 both sends signals, such as signal 304, and receives ultrasound response signals, such as ultrasound response signal 308.

As can be seen in FIG. 3, coupling material 313 couples transducer array 302 to structure 200. Coupling material 313 takes the form of water or any other desirable coupling material. Transducer array 302 sends signal 316 into coupling material 313. When signal 316 reaches surface 202 of structure 200, signal 316 refracts to cause signal 304 to enter structure 200 at angle 306. Angle 306 is a refraction angle. Angle 306 is related to the array steering angle for signal 316 by Snell's law. In some illustrative examples, the velocity of coupling material 313 is approximately half the velocity of structure 200. In these illustrative examples, angle 306 is roughly twice the array steering angle of signal 316.

Ultrasound response signal 308 is formed at second surface 204 of structure 200. In some illustrative examples, for ultrasonic inspections, second surface 204 may be referred to as back wall 310. Ultrasound response signal 308 is received at transducer array 302. Ultrasound response signal 308 has angle 312 relative to first surface 202. Angle 312 is a reflection of angle 306 about line 314 normal to first surface 202.

Ramp 210 forms an angle between zero and thirty degrees with line 314 normal to second surface 204. Ramp 212 forms an angle between zero and thirty degrees with line 314 normal to second surface 204.

As depicted, angle 306 and angle 312 are each greater than sixty degrees. Angle 306 and angle 312 are desirably greater than sixty degrees so that each of signal 304 and ultrasound response signal 308 are no more than thirty degrees relative to line 314 normal to first surface 202.

As depicted, when ultrasound response signal 308 reaches surface 202 of structure 200, ultrasound response signal 308 is refracted to form response signal 318. Transducer array 302 receives ultrasound response signal 308 in the form of response signal 318 from coupling material 313.

A porosity within structure 200 beneath ramp 210 can be detected from the amplitude of ultrasound response signal 308. The porosity within structure 200 along signal 304 may be detected using ultrasound response signal 308.

In some illustrative examples, to detect porosity using ultrasound response signal 308, porosity along signal 304 and porosity along ultrasound response signal 308 are assumed to be equal. In these illustrative examples, an average porosity along signal 304 and along ultrasound response signal 308 is evaluated from the signal strength. The signal strength in the presence of porosity would decrease when compared to a porosity free zone.

In some illustrative examples, porosity along ultrasound response signal 308 is known from previous inspections. In these illustrative examples, porosity along signal 304 is detected using ultrasound response signal 308 and the known porosity from previous inspections.

Ultrasound response signal 308 travels through structure 200 beneath second surface 204. A porosity within structure 200 along the path of ultrasound response signal 308 may be detected using ultrasound response signal 308.

Figure 4:
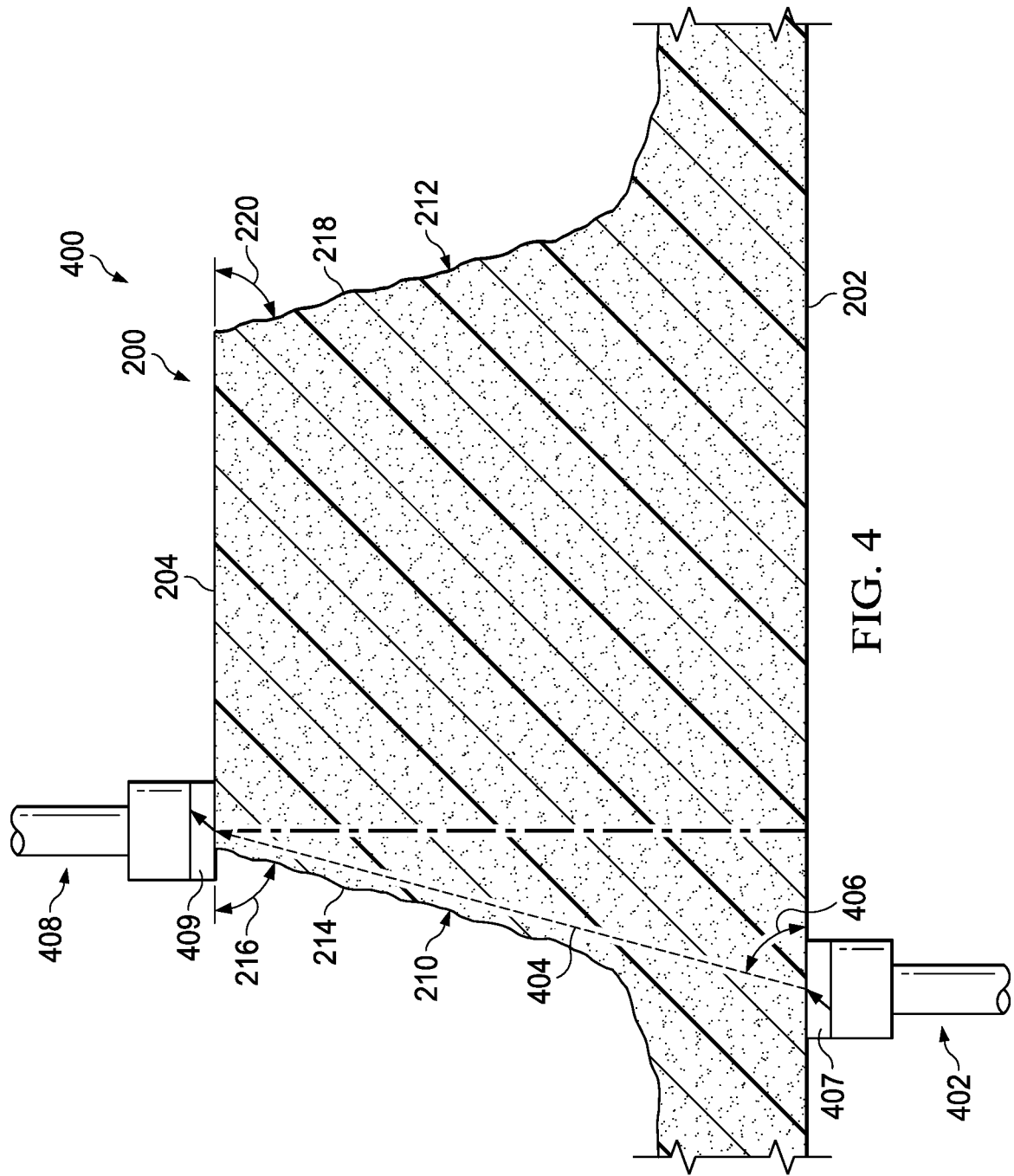
FIG. 4 is an illustration of a cross-sectional view of an ultrasonic inspection of a ramp of a composite structure in accordance with an illustrative embodiment.

Turning now to FIG. 4, an illustration of a cross-sectional view of an ultrasonic inspection of a ramp of a composite structure is depicted in accordance with an illustrative embodiment. View 400 is an illustration of an ultrasonic inspection of structure 200 of FIG. 2. In view 400, transmitter 402 sends signal 404 into first surface 202 of structure 200. Signal 404 is sent into structure 200 at angle 406 substantially parallel to ramp 210 of structure 200 using transmitter 402. As depicted, signal 404 is sent into structure 200 at angle 406 using electronic beam steering. In other non-depicted examples, signal 404 may be sent into structure 200 using a mechanical angle adjuster. Transmitter 402 is coupled to structure 200 using water 407 or other desirable coupling material.

Receiver 408 is positioned at second surface 204 of structure 200. Receiver 408 receives signal 404 at angle 406. An amplitude of signal 404 is used to detect a porosity within structure 200 beneath ramp 210. Porosity within structure 200 along signal 404 can be detected from the amplitude of signal 404. Receiver 408 is coupled to structure 200 using water 409 or other desirable coupling material.

Figure 5:
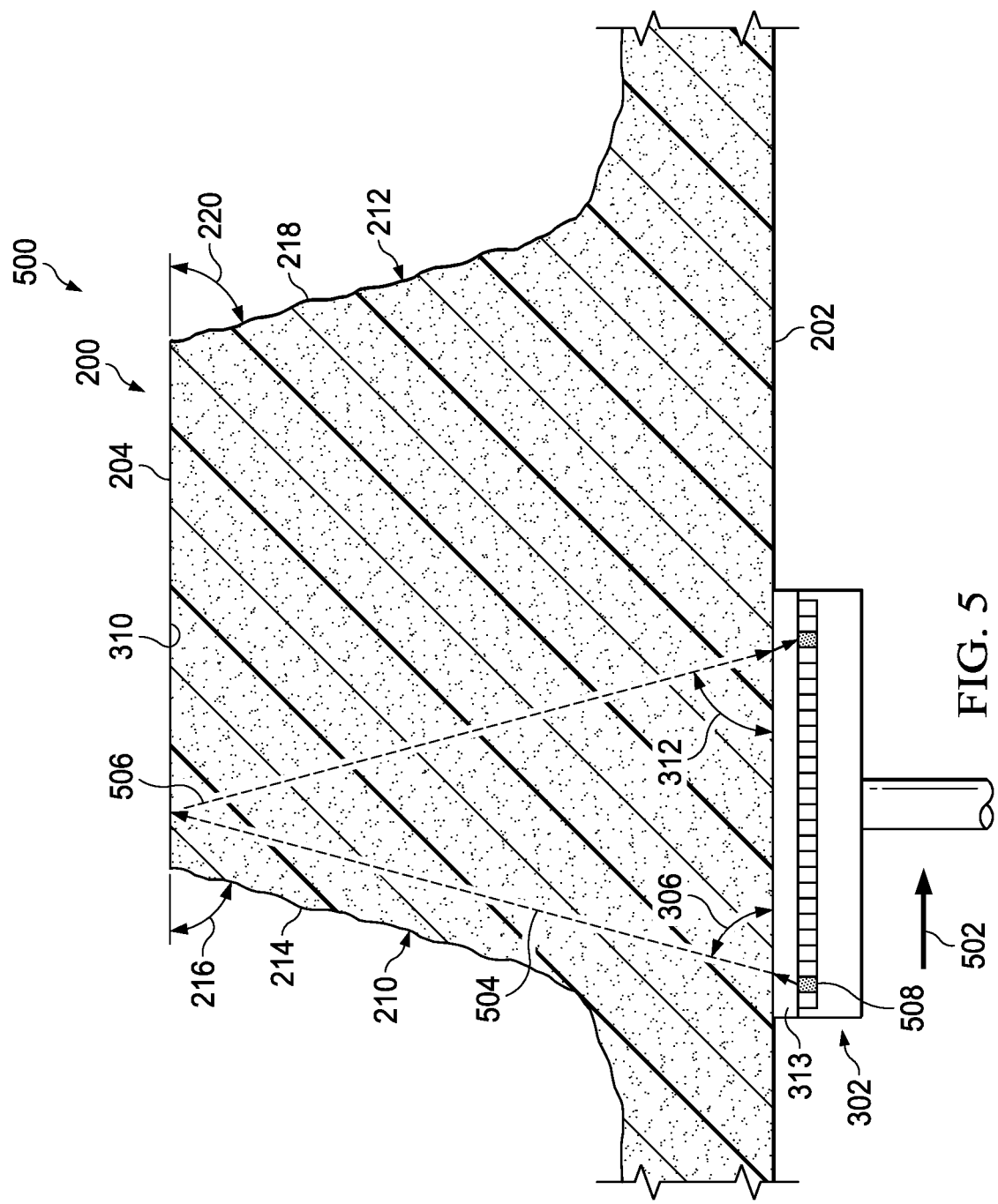
FIG. 5 is an illustration of a cross-sectional view of an ultrasonic inspection of a ramp of a composite structure in accordance with an illustrative embodiment.

Turning now to FIG. 5, an illustration of a cross-sectional view of an ultrasonic inspection of a ramp of a composite structure is depicted in accordance with an illustrative embodiment. In view 500, transducer array 302 has moved in direction 502 relative to structure 200.

After receiving ultrasound response signal 308 in FIG. 3, transducer array 302 sends another signal into structure 200 at angle 306 to detect a porosity within another portion of structure 200 beneath ramp 210. In view 500, transducer array 302 has moved in direction 502 after receiving ultrasound response signal 308 in FIG. 3.

In view 500, transducer array 302 sends signal 504 into structure 200 at angle 306. Angle 306 is substantially parallel to ramp 210 of structure 200. As depicted, signal 504 is sent into structure 200 at angle 306 using electronic beam steering.

Ultrasound response signal 506 is formed at second surface 204 of structure 200. Ultrasound response signal 506 is received at transducer array 302. Ultrasound response signal 506 has angle 312 relative to first surface 202. Angle 312 is a reflection of angle 306.

A porosity within structure 200 beneath ramp 210 can be detected from the amplitude of ultrasound response signal 506. The porosity within structure 200 along signal 504 may be detected using ultrasound response signal 506. In some illustrative examples, to detect porosity using ultrasound response signal 506, porosity along signal 504 and porosity along ultrasound response signal 506 are assumed to be equal. In these illustrative examples, an average porosity along signal 504 and along ultrasound response signal 506 is evaluated from the signal strength. The signal strength in the presence of porosity would decrease when compared to a porosity free zone.

In some illustrative examples, porosity along ultrasound response signal 506 is known from previous inspections. In these illustrative examples, porosity along signal 504 is detected using ultrasound response signal 506 and the known porosity from previous inspections.

Ultrasound response signal 506 travels through structure 200 beneath second surface 204. A porosity within structure 200 along the path of ultrasound response signal 506 may be detected using ultrasound response signal 506.

In this illustrative example, transducer array 302 may be moved in direction 502 prior to sending another signal into structure 200. In another illustrative example, a different transmitting cell of transducer array 302 sends a signal into structure 200. In this illustrative example, a transmitting cell in direction 502 from transmitting cell 508 sends another signal in structure 200. By using a different transmitting cell or moving transducer array 302, signals may be introduced in a pulsed fashion across the area beneath ramp 210.

Figure 6:
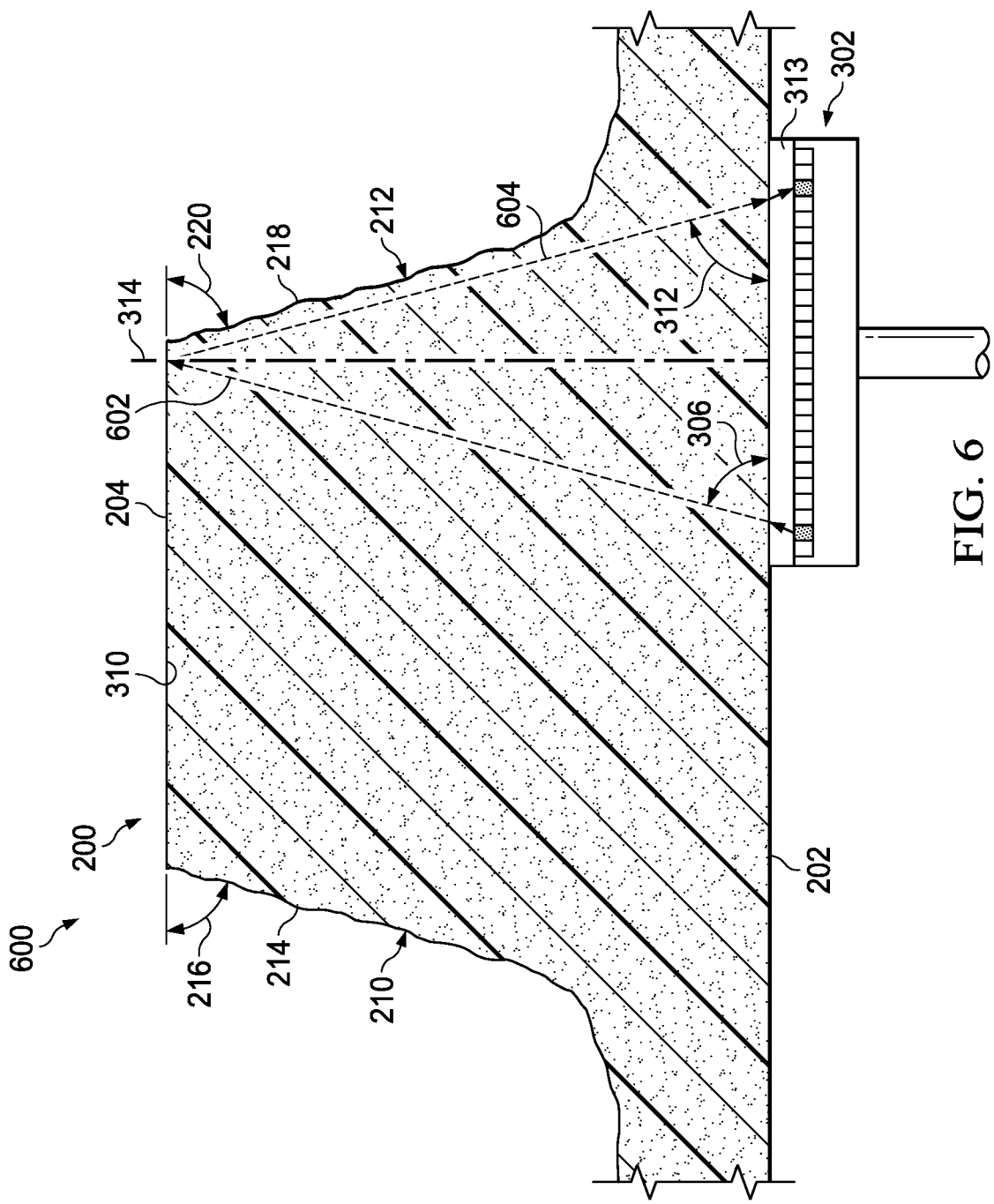
FIG. 6 is an illustration of a cross-sectional view of an ultrasonic inspection of a ramp of a composite structure in accordance with an illustrative embodiment.

Turning now to FIG. 6, an illustration of a cross-sectional view of an ultrasonic inspection of a ramp of a composite structure is depicted in accordance with an illustrative embodiment. In view 600, transducer array 302 has moved in direction 502 relative to structure 200.

In view 600, transducer array 302 sends signal 602 into structure 200 at angle 306. Signal 602 at angle 306 is substantially parallel to ramp 210 of structure 200. Ramp 210 is a reflection of ramp 212 about a line normal to first surface 202. The absolute values of angle 216 and angle 220 are substantially the same. Accordingly, signals with substantially the same angle, angle 306 could be sent into structure 200 to detect porosity under both ramp 210 and ramp 212.

As depicted, signal 602 at angle 306 is a reflection of ramp 212. As depicted, signal 602 is sent into structure 200 at angle 306 using electronic beam steering.

Ultrasound response signal 604 is formed at second surface 204 of structure 200. Ultrasound response signal 604 is received at transducer array 302. Ultrasound response signal 604 has angle 312 relative to first surface 202. Angle 312 is a reflection of angle 306. Ultrasound response signal 604 at angle 312 is substantially parallel to ramp 212 of structure 200.

A porosity within structure 200 beneath ramp 212 can be detected from the amplitude of ultrasound response signal 604. Ultrasound response signal 604 travels beneath ramp 212. The porosity within structure 200 along ultrasound response signal 604 may be detected using ultrasound response signal 604.

Signal 602 travels through structure 200 beneath second surface 204. A porosity within structure 200 along the path of signal 602 may be detected using ultrasound response signal 604.

In other non-depicted examples, transducer array 302 sends a signal having angle 312 relative to first surface 202 into structure 200. In these non-depicted examples, an ultrasound response signal having angle 306 is received at transducer array 302. In these non-depicted examples, signals parallel to ramp 212, also referred to as a second ramp, are used to detect porosity below ramp 212. In some illustrative examples, signals having angle 312 are used when ramp 212 and ramp 210 are not reflections of each other. For example, signals sent into structure 200 having angle 312 may be used to detect porosity beneath ramp 212 when angle 216 and angle 220 do not have the same absolute value.

In yet other non-depicted illustrative examples, transducer array 302 sends a signal having an angle that is a reflection of ramp 212 into structure 200 to detect porosity within structure 200 beneath ramp 212, in which the angle is different from the angle of signals used to inspect ramp 210. For example, when angle 216 and 220 do not have the same absolute value, amplitudes of ultrasound response signals parallel to ramp 212 may be used to detect porosity. In these examples, the ultrasound response signals do not have angle 312.

The different components shown in FIGS. 2-6 may be combined with components in FIG. 1, used with components in FIG. 1, or a combination of the two. Additionally, some of the components in FIGS. 2-6 may be illustrative examples of how components shown in block form in FIG. 1 can be implemented as physical structures.

Figure 7:
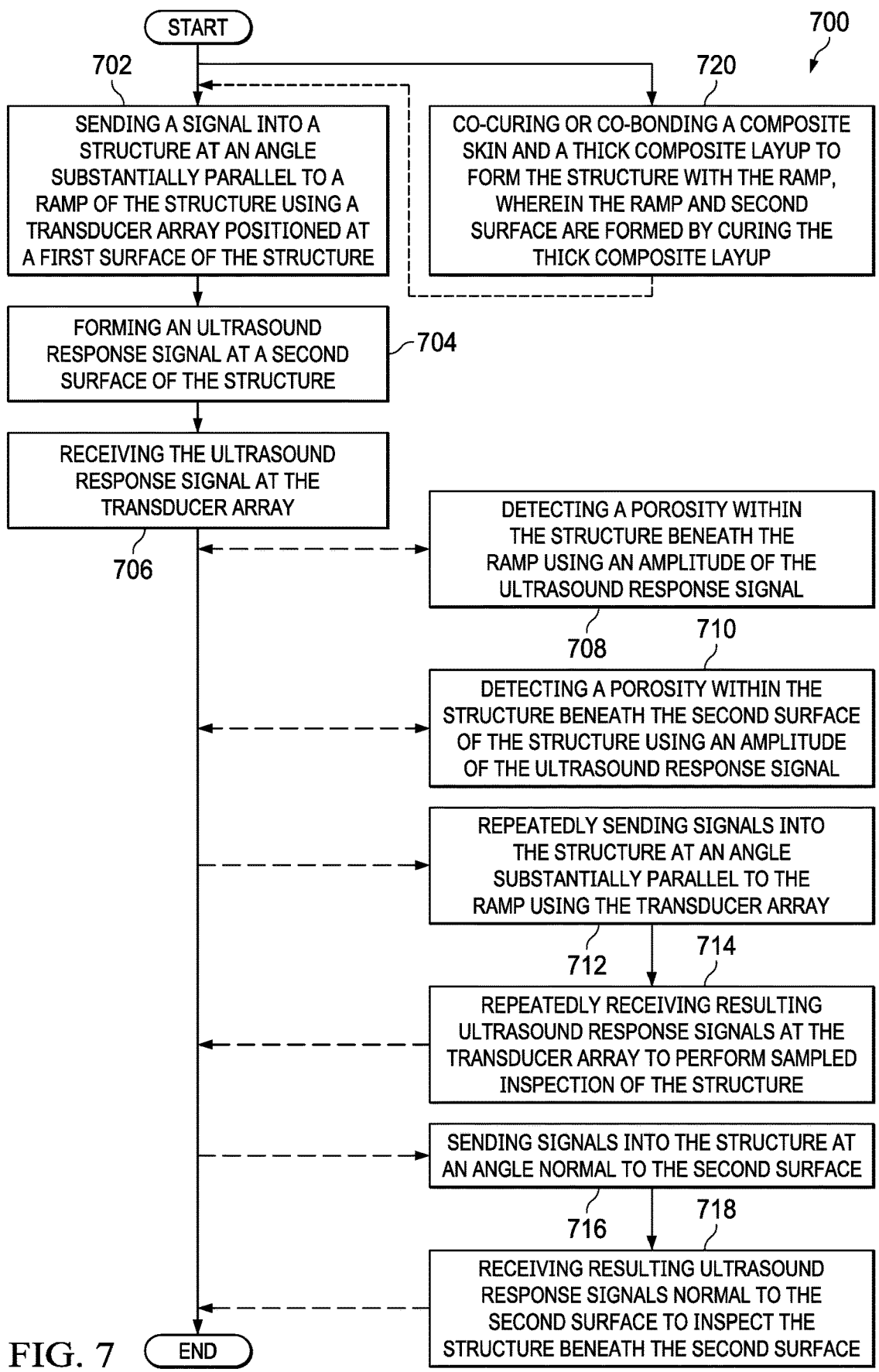
FIG. 7 is an illustration of a flowchart of a method for inspecting a structure using ultrasonic techniques in accordance with an illustrative embodiment.

Turning now to FIG. 7, an illustration of a flowchart of a method for inspecting a structure using ultrasonic techniques is depicted in accordance with an illustrative embodiment. Method 700 may be implemented in inspection environment 100 of FIG. 1. Method 700 may be implemented on structure 200 of FIGS. 2-6.

Method 700 sends a signal into a structure at an angle substantially parallel to a ramp of the structure using a transducer array positioned at a first surface of the structure (operation 702). In some illustrative examples, the structure comprises a composite material. In some illustrative examples, the ramp forms an angle between zero and thirty degrees with a line normal to the second surface. In some illustrative examples, the ramp has significant surface variation in average surface roughness.

Method forms an ultrasound response signal at a second surface of the structure (operation 704). Method 700 receives the ultrasound response signal at the transducer array (operation 706).

In some illustrative examples, method 700 detects a porosity within the structure beneath the ramp using an amplitude of the ultrasound response signal (operation 708). In some illustrative examples, method 700 detects a porosity within the structure beneath the second surface of the structure using an amplitude of the ultrasound response signal (operation 710).

In some illustrative examples, method 700 repeatedly sends signals into the structure at an angle substantially parallel to the ramp using the transducer array (operation 712). In these illustrative examples, method 700 repeatedly receives resulting ultrasound response signals at the transducer array to perform sampled inspection of the structure (operation 714).

In some illustrative examples, method 700 also sends signals into the structure at an angle normal to the second surface (operation 716). In these illustrative examples, method 700 receives resulting ultrasound response signals normal to the second surface to inspect the structure beneath the second surface (operation 718).

The structure may optionally be formed as part of method 700. In some illustrative examples, method 700 co-cures or co-bonds a composite skin and a thick composite layup to form the structure with the ramp, wherein the ramp and second surface are formed by curing the thick composite layup (operation 720). The composite skin and the thick composite layup may be formed in any desirable fashion. In some illustrative examples, a plurality of composite plies is laid up to form a composite skin. In some illustrative examples, a second plurality of composite plies of varying widths are laid up to form a thick composite layup.

As depicted, operations 708 through 724 are optional. Operations 708 through 724 may occur in some illustrative examples and be absent in others.

Figure 8:
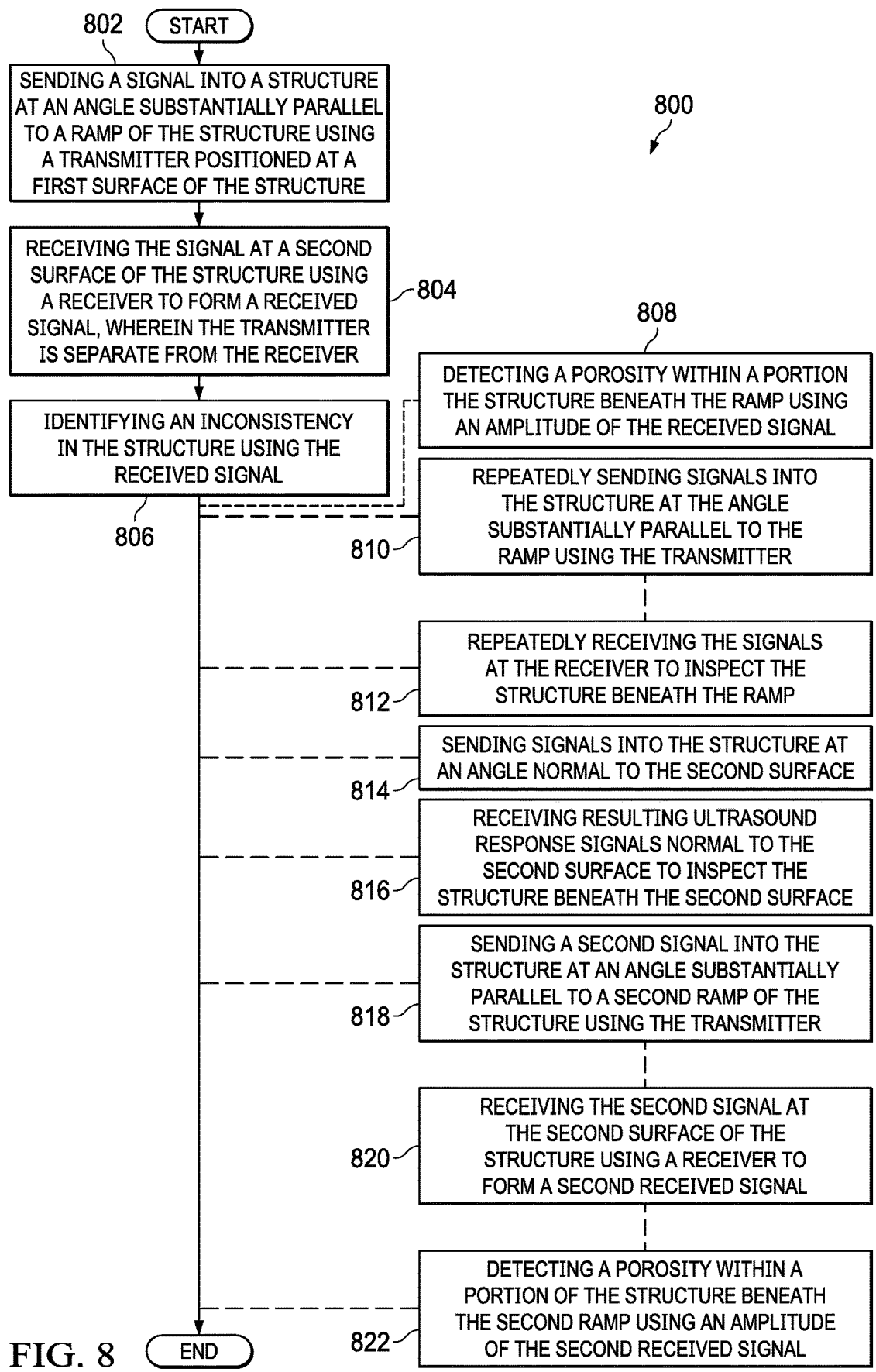
FIG. 8 is an illustration of a flowchart of a method for inspecting a structure using ultrasonic techniques in accordance with an illustrative embodiment.

Turning now to FIG. 8, an illustration of a flowchart of a method for inspecting a structure using ultrasonic techniques is depicted in accordance with an illustrative embodiment. Method 800 may be implemented in inspection environment 100 of FIG. 1. Method 800 may be implemented on structure 200 of FIGS. 2-6.

Method 800 sends a signal into a structure at an angle substantially parallel to a ramp of the structure using a transmitter positioned at a first surface of the structure (operation 802). Sending the signal into the structure at the angle comprises steering a beam using one of a mechanical angle adjuster or electronic beam steering. In some illustrative examples, the structure comprises a composite material. In some illustrative examples, the ramp forms an angle between zero and thirty degrees with a line normal to the second surface.

Method 800 receives the signal at a second surface of the structure using a receiver to form a received signal, wherein the transmitter is separate from the receiver (operation 804). Method 800 identifies an inconsistency in the structure using the received signal (operation 806).

In some illustrative examples, method 800 detects a porosity within a portion the structure beneath the ramp using an amplitude of the received signal (operation 808). In some illustrative examples, method 800 repeatedly sends signals into the structure at the angle substantially parallel to the ramp using the transmitter (operation 810). In some illustrative examples, method 800 repeatedly receives the signals at the receiver to inspect the structure beneath the ramp (operation 812).

In some illustrative examples, method 800 sends signals into the structure at an angle normal to the second surface (operation 814). In some illustrative examples, method 800 receives resulting ultrasound response signals normal to the second surface to inspect the structure beneath the second surface (operation 816).

In some illustrative examples, method 800 sends a second signal into the structure at an angle substantially parallel to a second ramp of the structure using the transmitter (operation 818). In some illustrative examples, method 800 receives the second signal at the second surface of the structure using a receiver to form a second received signal (operation 820). In some illustrative examples, method 800 detects a porosity within a portion the structure beneath the second ramp using an amplitude of the second received signal (operation 822).

As depicted, operations 808 through 822 are optional. Operations 808 through 822 may occur in some illustrative examples and be absent in others.

Figure 9:
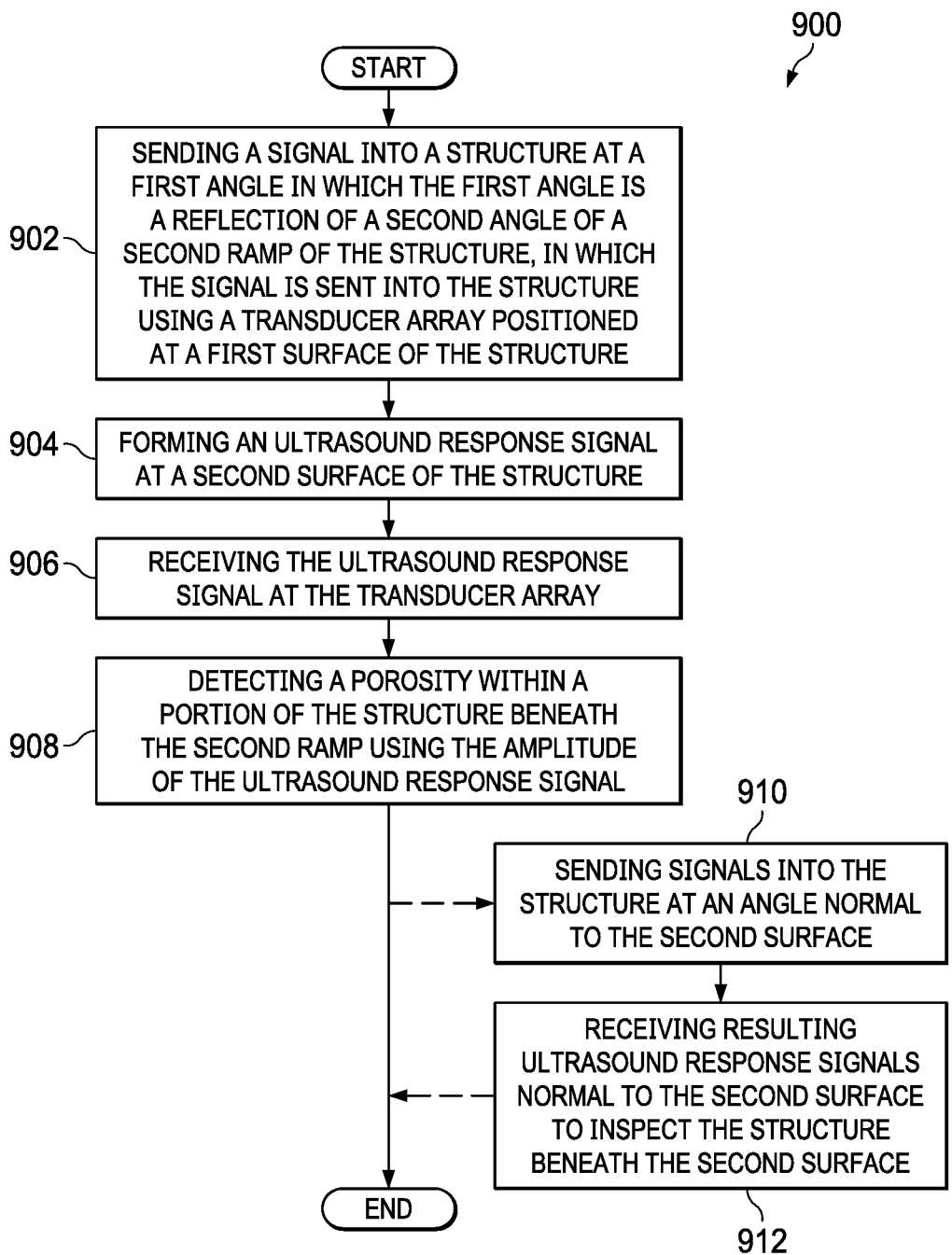
FIG. 9 is an illustration of a flowchart of a method for inspecting a structure using ultrasonic techniques in accordance with an illustrative embodiment.

Turning now to FIG. 9, an illustration of a flowchart of a method for inspecting a structure using ultrasonic techniques is depicted in accordance with an illustrative embodiment. Method 900 may be implemented in inspection environment 100 of FIG. 1. Method 900 may be implemented on structure 200 of FIGS. 2-6.

Method 900 sends a signal into a structure at a first angle in which the first angle is a reflection of a second angle of a second ramp of the structure, in which the signal is sent into the structure using a transducer array positioned at a first surface of the structure (operation 902). In some illustrative examples, the second ramp forms an angle between zero and thirty degrees with a line normal to the second surface.

Method 900 forms an ultrasound response signal at a second surface of the structure (operation 904).

Method 900 receives an ultrasound response signal at the transducer array (operation 906). Method 900 detects a porosity within a portion of the structure beneath the second ramp using the amplitude of the ultrasound response signal (operation 908). Afterwards the method terminates.

In some illustrative examples, method 900 sends signals into the structure at an angle normal to the second surface (operation 910). In these illustrative examples, method 900 receives resulting ultrasound response signals normal to the second surface to inspect the structure beneath the second surface (operation 912).

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added, in addition to the illustrated blocks, in a flowchart or block diagram.

The illustrative examples provide methods in which an ultrasound beam is steered parallel to the ramp that is being inspected rather than perpendicular to the surface. The illustrative examples could be performed in pitch catch or through transmission. The illustrative examples direct the sending signal up to and adjacent to the ramp surface. The illustrative examples provide desirable sensitivity to inconsistencies in the ramp.

In some illustrative examples, inspections using beam steering parallel to a ramp are combined with inspection using traditional non-beam steering path. By combining the beam steering with normal signals in traditional ultrasonic inspections, a desirable coverage of composite structure is obtained. In these illustrative examples, the traditional normal ultrasonic paths are used to inspect for inconsistencies that are parallel to the top of the part surface. Further, traditional normal ultrasonic paths may be used to inspect for inconsistencies, such as wrinkles, beneath a parallel back surface.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method comprising:
   sending a signal into a structure at an angle substantially parallel to a ramp of the structure using a transducer array positioned at a first surface of the structure;
   forming an ultrasound response signal at a second surface of the structure; and
   receiving the ultrasound response signal at the transducer array; and
   detecting a porosity within the structure beneath the second surface of the structure using an amplitude of the ultrasound response signal.

2. The method of claim 1 further comprising:
   detecting a second porosity within the structure beneath the ramp using the amplitude of the ultrasound response signal.

3. The method of claim 1 further comprising:
   repeatedly sending signals into the structure at an angle substantially parallel to the ramp using the transducer array; and
   repeatedly receiving resulting ultrasound response signals at the transducer array to perform sampled inspection of the structure.

4. The method of claim 1 further comprising:
   sending signals into the structure at an angle normal to the second surface; and
   receiving resulting ultrasound response signals normal to the second surface to inspect the structure beneath the second surface.

5. The method of claim 1, wherein the structure comprises a composite material.

6. The method of claim 5 further comprising:
   co-curing or co-bonding a composite skin and a thick composite layup to form the structure with the ramp, wherein the ramp and second surface are formed by curing the thick composite layup.

7. The method of claim 1, wherein the ramp forms an angle between zero and thirty degrees with a line normal to the second surface.

8. A method comprising:
   sending a signal into a structure using a transducer array positioned at a first surface of the structure;
   forming an ultrasound response signal at a second surface of the structure in which the ultrasound response signal is parallel to a ramp and travels beneath the ramp;
   receiving the ultrasound response signal at the transducer array; and
   detecting a porosity within a portion of the structure beneath the ramp using an amplitude of the ultrasound response signal.

9. The method of claim 8, wherein the ramp forms an angle between zero and thirty degrees with a line normal to the second surface.

10. The method of claim 8 further comprising:
    sending signals into the structure at an angle normal to the second surface; and
    receiving resulting ultrasound response signals normal to the second surface to inspect the structure beneath the second surface.

11. The method of claim 8, wherein the structure comprises a composite material.

12. The method of claim 8 further comprising:
    repeatedly sending signals into the structure using the transducer array; and
    repeatedly receiving resulting ultrasound response signals at the transducer array to perform sampled inspection of the structure.

13. The method of claim 8 further comprising:
    co-curing or co-bonding a composite skin and a thick composite layup to form the structure with the ramp, wherein the ramp and second surface are formed by curing the thick composite layup.

14. A method comprising:
sending a signal into a structure at an angle substantially parallel to a ramp of the structure using a transducer array positioned at a first surface of the structure;
forming an ultrasound response signal at a second surface of the structure;
receiving the ultrasound response signal at the transducer array;
sending signals into the structure at an angle normal to the second surface; and
receiving resulting ultrasound response signals normal to the second surface to inspect the structure beneath the second surface.

15. The method of claim 14 further comprising:
detecting a porosity within the structure beneath the ramp using an amplitude of the ultrasound response signal.

16. The method of claim 14 further comprising:
detecting a porosity within the structure beneath the second surface of the structure using an amplitude of the ultrasound response signal.

17. The method of claim 14 further comprising:
repeatedly sending signals into the structure at an angle substantially parallel to the ramp using the transducer array; and
repeatedly receiving resulting ultrasound response signals at the transducer array to perform sampled inspection of the structure.

18. The method of claim 14, wherein the structure comprises a composite material.

19. The method of claim 18 further comprising:
co-curing or co-bonding a composite skin and a thick composite layup to form the structure with the ramp, wherein the ramp and second surface are formed by curing the thick composite layup.

20. The method of claim 14, wherein the ramp forms an angle between zero and thirty degrees with a line normal to the second surface.

* * * * *